(12) United States Patent
Kawanishi et al.

(10) Patent No.: US 7,469,574 B2
(45) Date of Patent: Dec. 30, 2008

(54) LIQUID TYPE IDENTIFYING METHOD AND LIQUID TYPE IDENTIFYING DEVICE

(75) Inventors: Toshiaki Kawanishi, Ageo (JP); Akiko Kubota, Ageo (JP); Kiyoshi Yamagishi, Ageo (JP)

(73) Assignee: Mitsui Mining & Smelting Co., Ltd., Tokyo (JP)

( * ) Notice: Subject to any disclaimer, the term of this patent is extended or adjusted under 35 U.S.C. 154(b) by 103 days.

(21) Appl. No.: 11/597,847

(22) PCT Filed: May 17, 2005

(86) PCT No.: PCT/JP2005/008946

§ 371 (c)(1),
(2), (4) Date: Nov. 27, 2006

(87) PCT Pub. No.: WO2005/116620

PCT Pub. Date: Dec. 8, 2005

(65) Prior Publication Data

US 2008/0066531 A1    Mar. 20, 2008

(30) Foreign Application Priority Data

May 28, 2004    (JP)    ............................. 2004-159334

(51) Int. Cl.
*G01N 25/00* (2006.01)
(52) U.S. Cl. .................................................. 73/61.46
(58) Field of Classification Search ................ 73/61.46, 73/61.76
See application file for complete search history.

(56) References Cited

U.S. PATENT DOCUMENTS

| | | | | |
|---|---|---|---|---|
| 3,264,862 A | * | 8/1966 | Felton et al. ............... | 73/25.01 |
| 3,498,113 A | * | 3/1970 | Whatley ..................... | 73/61.76 |
| 3,552,207 A | * | 1/1971 | Monk et al. ................. | 374/31 |
| 3,726,126 A | * | 4/1973 | De Vittorio ................. | 73/61.76 |
| 4,062,223 A | * | 12/1977 | Lamphere et al. .......... | 73/25.01 |
| 4,116,045 A | * | 9/1978 | Potter ......................... | 73/61.46 |
| 4,226,114 A | * | 10/1980 | Hagedorn ................... | 73/61.76 |
| 4,250,738 A | * | 2/1981 | Huch ........................... | 374/45 |
| 4,251,809 A | * | 2/1981 | Cheney ....................... | 340/603 |
| 5,225,334 A | * | 7/1993 | Tanno et al. ................. | 435/39 |

(Continued)

FOREIGN PATENT DOCUMENTS

JP    5-33712    8/1993

(Continued)

*Primary Examiner*—Hezron E. Williams
*Assistant Examiner*—John Fitzgerald
(74) *Attorney, Agent, or Firm*—Frommer Lawrence & Haug LLP; Ronald R. Santucci

(57) ABSTRACT

A liquid type identifying method and device for correctly and quickly determining whether or not a liquid is a predetermined one. An identifying sensor unit (2) so disposed as to face a flow passage (24) of a liquid to be measured has an indirect-heating liquid type detecting section (21) including a heater and a heat sensor and a liquid temperature sensing section (22). A single pulse voltage is applied to the heater of the liquid type detecting section to allow the heater to generate heat, and an identification calculation section makes an identification according to the output of the liquid type detecting circuit including the heat sensor of the liquid type detecting section and the liquid temperature sensing section.

17 Claims, 13 Drawing Sheets

U.S. PATENT DOCUMENTS

| | | | |
|---|---|---|---|
| 5,415,024 A * | 5/1995 | Proffitt et al. | 73/61.44 |
| 5,518,933 A * | 5/1996 | Ishibashi | 436/163 |
| 6,739,178 B2 * | 5/2004 | Dimarzo et al. | 73/25.01 |
| 7,036,356 B2 * | 5/2006 | Leppanen et al. | 73/61.43 |
| 7,152,582 B2 * | 12/2006 | Takahata et al. | 123/406.12 |
| 7,168,300 B2 * | 1/2007 | Kawanishi et al. | 73/61.46 |
| 7,367,711 B2 * | 5/2008 | Kawanishi et al. | 374/45 |

FOREIGN PATENT DOCUMENTS

| | | |
|---|---|---|
| JP | 11-153561 | 6/1999 |
| JP | 2001-020724 A | 1/2001 |
| JP | 2004-101385 A | 4/2004 |
| JP | 2005-214856 | 8/2005 |
| WO | WO 2005/026710 A | 3/2005 |

* cited by examiner

LIQUID TYPE IDENTIFYING METHOD AND LIQUID TYPE IDENTIFYING DEVICE

This application is a 371 of PCT/JP2005/008946 filed on May 17, 2005, published on Dec. 8, 2005 under publication number WO 2005/116620 A1 which claims priority benefits from Japanese Patent Application Number 2004-159334 filed May 28, 2004.

TECHNICAL FIELD

The present invention relates to a liquid type identifying method and liquid type identifying device which use thermal properties of liquid to determine whether or not a liquid is a predetermined one.

A method and device for identifying liquid type according to the present invention can be used for determining whether or not a liquid that is sprayed as urea solution having a predetermined urea concentration to an exhaust gas purification catalyst for decomposition of nitrogen oxide (NOx) in a system for purifying exhaust gas emitted from an internal-combustion engine of, e.g., a car is actually the urea solution having a predetermined urea concentration.

BACKGROUND ART

In an internal-combustion engine of a car, fossil fuels such as gasoline or light-oil are burned. Exhaust gas generated by the burning contains water and carbon dioxide, as well as environmental pollutants such as unburned carbon monoxide (CO), unburned carbon hydride (HC), sulfur oxide (SOx), and nitrogen oxide (NOx). In recent years, various countermeasures to purify the car exhaust gas have been taken especially for environmental protection and prevention of living environment pollution.

As one of such countermeasures, a use of an exhaust gas purification catalyst unit can be exemplified. Specifically, a three-way catalyst for exhaust gas purification is disposed in the middle of an exhaust system, and, there, CO, HC, NOx, etc. are decomposed by oxidation-reduction process to thereby render the above environmental pollutants harmless. In order to maintain the decomposition of NOx in the catalyst unit, urea solution is sprayed to the catalyst from upstream side of the catalyst unit in the exhaust system. In order to enhance the rate of decomposition of NOx, urea concentration of the urea solution should fall within a specified range, and a urea concentration of 32.5% is considered to be optimum.

The urea solution is stored in a urea solution tank installed in a car. In this state, however, concentration may change with time, or unevenness in the concentration distribution may locally occur in the tank. The urea solution which is supplied from the tank to a spray nozzle through a supply pipe by means of a pump is taken from the outlet provided near the bottom portion of the tank in general. Therefore, it is important for the urea solution in such an area to have a predetermined urea concentration, in order to enhance the efficiency of the catalyst unit.

Further, it could be that a liquid other than the urea solution is accidentally introduced into the urea solution tank under present circumstances. In such a case, it is necessary to quickly detect that the liquid is a solution other than the urea solution having a predetermined urea concentration so as to issue an alarm, in order for the catalyst unit to fulfill its capability.

Conventionally, measurement of the concentration of urea in the urea solution has not directly been made. Meanwhile, a technique that uses NOx sensors disposed respectively on the upstream and downstream sides of the catalyst unit in the exhaust system has been made. In this technique, it is determined whether optimum decomposition of NOx has been carried out based on the difference in NOx concentration detected by these sensors. However, this technique aims at measuring the effect of a reduction in the amount of NOx and therefore cannot determine whether or not the liquid is urea solution having a predetermined urea concentration even at the beginning of the spray of urea solution as well as before the spray. Further, the NOx sensor used in such a technique did not have sufficient sensitivity for ensuring spray of urea solution having a urea concentration falling within a predetermined range.

JP-A-11-153561 discloses a fluid identifying method. In this method, a current is applied to heat a heater, and the heat generated is used to heat a temperature sensor. Then, thermal influence is applied to heat transfer from the heater to temperature sensor using a fluid to be identified and, based on an electrical output value of the temperature sensor which corresponds to a resistance value, the type of the fluid to be identified is determined. The application of a current to the heater is periodically performed in this method.

However, since the current application to the heater is periodically performed (that is, current is applied with a large number of pulses) in the fluid identifying method, it takes time to carry out the identification processing. That is, it is difficult to identify the type of a fluid at short times. Further, although this method can distinguish among substances (e.g., water, air, and oil) having properties largely different from each other using representative values, it has difficulty determining whether or not the solution as described above is urea solution having a predetermined urea concentration correctly and quickly.

DISCLOSURE OF INVENTION

The present invention has been made in view of the above situation, and an object thereof is to provide a liquid type identifying method and liquid type identifying device capable of determining whether or not a liquid is a predetermined one correctly and quickly.

To solve the above problem, according to the present invention, there is provided a liquid type identifying method, wherein a single pulse voltage is applied to a heater disposed to face a liquid to be measured to allow the heater to generate heat, and it is determined whether or not the liquid to be measured is a predetermined one based on a combination of a liquid-type-corresponding first voltage value corresponding to a difference between an initial temperature of a temperature sensor disposed to face the liquid to be measured and a first temperature thereof obtained at the time point after a first time period has elapsed from a start of application of the single pulse voltage and liquid-type-corresponding second voltage value corresponding to a difference between the initial temperature of the temperature sensor and a second temperature thereof obtained at the time point after a second time period, which is longer than the first time period, has elapsed from the start of application of the single pulse voltage.

In an aspect of the present invention, it is determined that the liquid to be measured is the predetermined one only when both the liquid-type-corresponding first voltage value and liquid-type-corresponding second voltage value fall within their respective predetermined ranges and, otherwise, it is determined that the liquid to be measured is not the predetermined one. In an aspect of the present invention, the predetermined range of the liquid-type-corresponding first voltage value and that of the liquid-type-corresponding second voltage value change depending on a temperature of the liquid to be measured. In an aspect of the present invention, the liquid-type-corresponding first voltage value and liquid-type-corresponding second voltage value are obtained based on outputs of a liquid type detecting circuit including both the temperature sensor and a liquid temperature detecting section for detecting a temperature of the liquid to be measured.

In an aspect of the present invention, an average initial voltage value which is obtained by sampling an initial voltage predetermined number of times before the start of application of the single pulse to the heater and averaging them is used as a voltage value corresponding to the initial temperature of the temperature sensor, an average first voltage value which is obtained by sampling a first voltage at the time after the first time period has elapsed from the start of application of the single pulse to the heater predetermined number of times and averaging them is used as a voltage value corresponding to the first temperature of the temperature sensor, an average second voltage value which is obtained by sampling a second voltage at the time after the second time period has elapsed from the start of application of the single pulse to the heater predetermined number of times and averaging them is used as a voltage value corresponding to the second temperature of the temperature sensor, a difference between the average first voltage value and average initial voltage value is used as the liquid-type-corresponding first voltage value, and a difference between the average second voltage value and average initial voltage value is used as the liquid-type-corresponding second voltage value.

In an aspect of the present invention, the predetermined liquid is urea solution having a urea concentration falling within a predetermined range. In an aspect of the present invention, a first calibration curve or second calibration curve indicating a relationship between the temperature and liquid-type-corresponding first voltage value or liquid-type-corresponding second voltage value with respect to urea solutions having different urea concentrations is prepared and, when the liquid to be measured is determined to be urea solution having a urea concentration falling within a predetermined range, the urea concentration of the urea solution is calculated based on an output of a liquid temperature detecting section for detecting the temperature of the liquid to be measured, liquid-type-corresponding first voltage value or liquid-type-corresponding second voltage value, and first or second calibration curve.

To solve the above problem, according to the present invention, there is also provided a liquid type identifying device for determining whether a liquid to be measured is a predetermined one, comprising:

an identifying sensor section disposed to face a flow passage of the liquid to be measured, the identifying sensor section having both an indirect-heating liquid type detection section including a heater and temperature sensor and a liquid temperature detecting section for detecting the temperature of the liquid to be measured; and an identifying calculation section which applies a single pulse voltage to the heater of the indirect-heating liquid type detection section to allow the heater to generate heat and identifies the type of the liquid to be measured based on outputs of a liquid type detecting circuit including both the temperature sensor of the indirect-heating liquid type detection section and the liquid temperature detecting section, wherein the identifying calculation section determines whether or not the liquid to be measured is the predetermined one based on a combination of a liquid-type-corresponding first voltage value corresponding to a difference between an initial temperature of the temperature sensor and a first temperature thereof obtained at the time point after a first time period has elapsed from a start of application of the single pulse voltage and liquid-type-corresponding second voltage value corresponding to a difference between the initial temperature of the temperature sensor and a second temperature thereof obtained at the time point after a second time period, which is longer than the first time period, has elapsed from the start of application of the single pulse voltage.

In an aspect of the present invention, the predetermined liquid is urea solution having a urea concentration falling within a predetermined range. In an aspect of the present invention, a liquid-temperature-corresponding output value corresponding to the temperature of the liquid to be measured is input from the liquid temperature detecting section to the identifying calculation section, and the identifying calculation section uses a first calibration curve or second calibration curve indicating a relationship between the temperature of the liquid to be measured and liquid-type-corresponding first voltage value or liquid-type-corresponding second voltage value with respect to urea solutions having different urea concentrations to calculate the urea concentration of the urea solution assuming that the liquid to be measured is the urea solution having a urea concentration falling within a predetermined range, and wherein the urea concentration is calculated based on the liquid-temperature-corresponding output value obtained with respect to the liquid to be measured, liquid-type-corresponding first voltage value or liquid-type-corresponding second voltage value, and first or second calibration curve.

In an aspect of the present invention, the indirect-heating liquid type detection section and liquid temperature detecting section have a heat transfer member for liquid type detection section and a heat transfer member for liquid temperature detecting section for heat exchange with the liquid to be measured, respectively.

In the present invention, with a single pulse voltage applied to a heater to allow the heater to generate heat, it is determined whether or not the liquid to be measured is a predetermined one based on a combination of a liquid-type-corresponding first voltage value corresponding to a difference between the initial temperature of a temperature sensor and a first temperature thereof obtained at the time point after a first time period has elapsed from the start of the single pulse voltage application and liquid-type-corresponding second voltage value corresponding to a difference between the initial temperature of the temperature sensor and a second temperature thereof obtained at the time point after a second time period has elapsed from the start of the single pulse voltage application. Based on this method, it can be determined that the liquid to be measured is the predetermined one only when both the liquid-type-corresponding first voltage value and liquid-type-corresponding second voltage value fall within their respective predetermined ranges and, otherwise, it can be determined that the liquid to be measured is not the predetermined one. Thus, it is possible to determine whether or not the liquid to be measured is the predetermined one correctly and quickly.

By appropriately changing the predetermined ranges of the liquid-type-corresponding first voltage value and that of the liquid-type-corresponding second voltage value depending on the temperature of the liquid to be measured, it is possible to make the above determination more correctly.

BEST MODE FOR CARRYING OUT THE INVENTION

Embodiments of the present invention will be described below with reference to the accompanying drawings.

Figure 1:
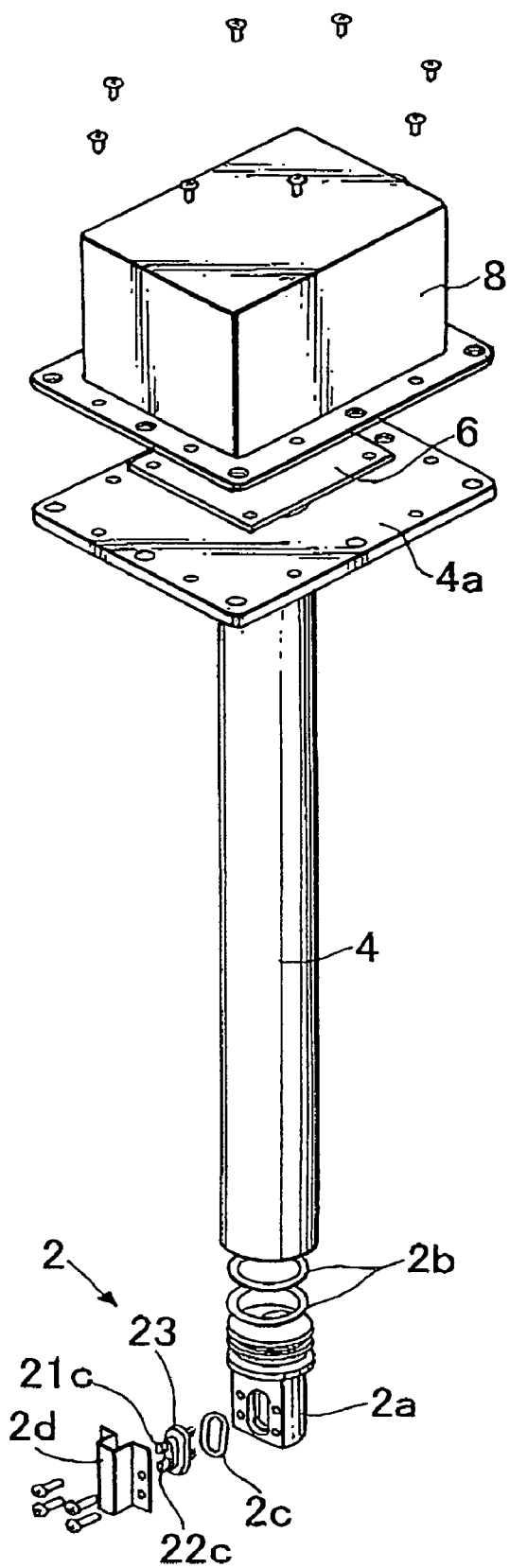
FIG. 1 is an exploded perspective view showing an embodiment of a liquid type identifying device according to the present invention.
Figure 2:
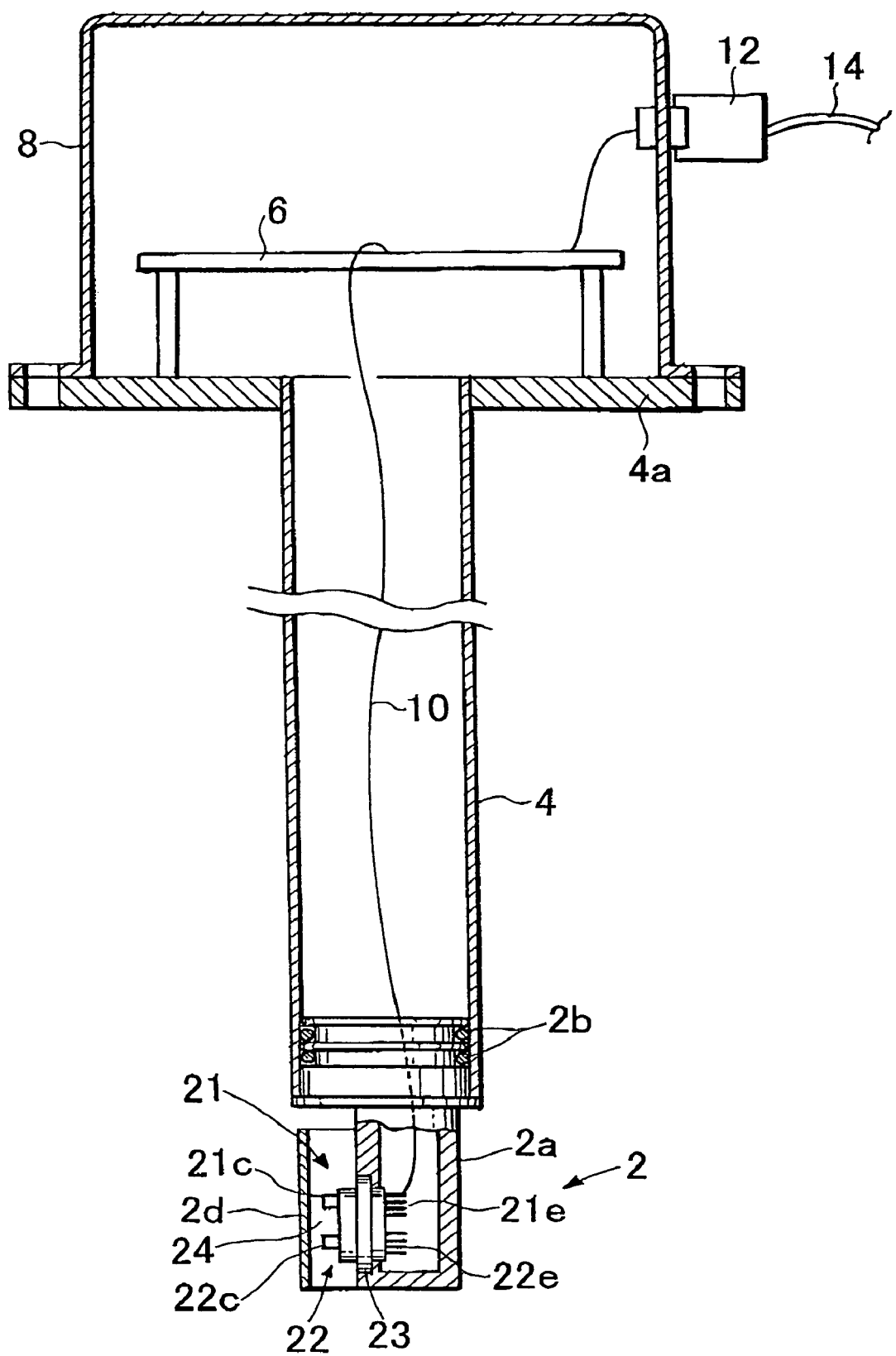
FIG. 2 is a partly omitted cross-sectional view of the liquid type identifying device of FIG. 1.
Figure 3:
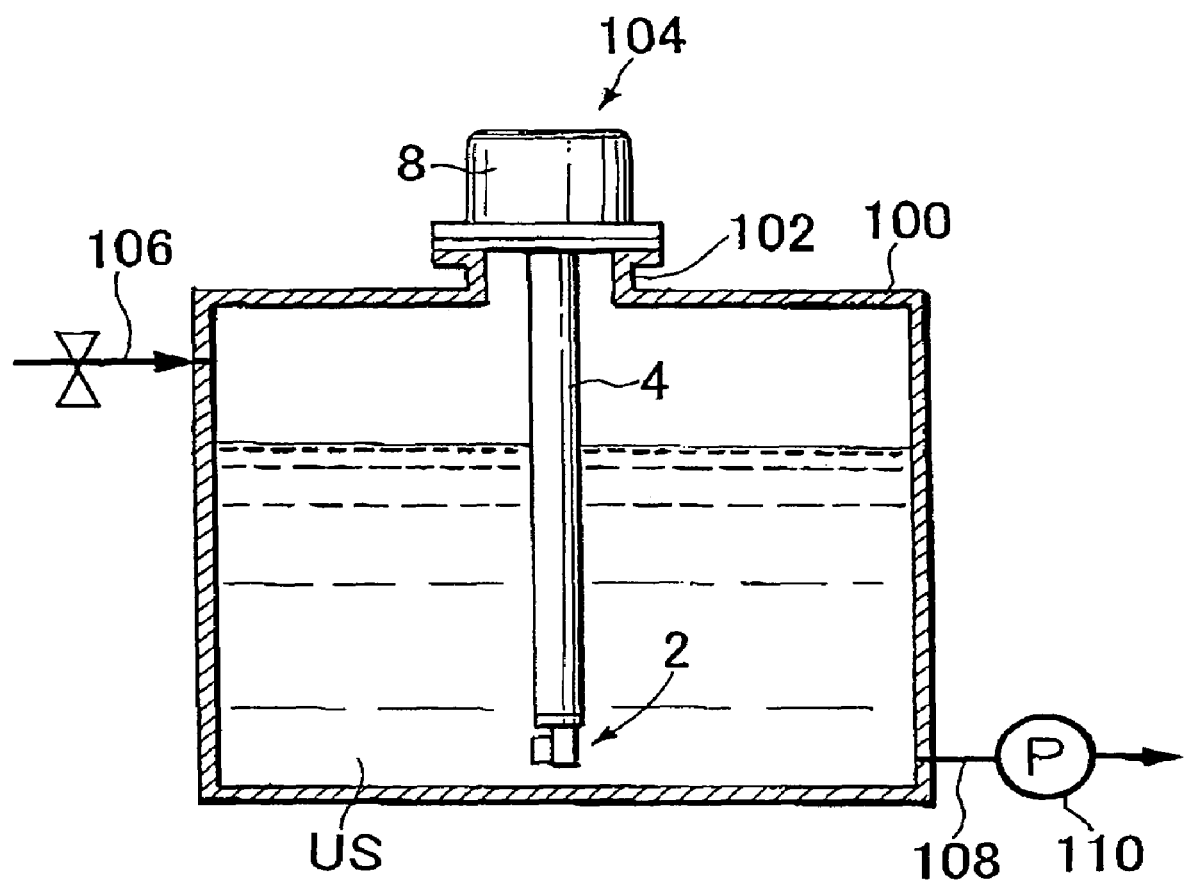
FIG. 3 is a view showing a state where the liquid type identifying device has been set to a tank.

FIG. 1 is an exploded perspective view showing an embodiment of a liquid type identifying device according to the present invention. FIG. 2 is a partly omitted cross-sectional view of the liquid type identifying device. FIG. 3 is a view showing a state where the liquid type identifying device has been set to a tank. In the present embodiment, urea solution having a urea concentration falling within a predetermined range is used as a predetermined solution.

As shown in FIG. 3, a urea solution tank 100 for NOx decomposition that constitutes an exhaust gas purification system installed in, e.g., a car has, at its upper portion, opening 102. A liquid type identifying device 104 according to the present invention is fitted to the opening 102. The urea solution tank 100 is connected to both an inlet piping 106 through which the urea solution is introduced into the tank and an outlet piping 108 through which the urea solution is discharged from the tank. The outlet piping 108 is connected to the tank at substantially the same height position as the bottom line of the tank 100, and starts from the outlet of the tank 100 to a not shown urea solution sprayer through a urea solution supply pump 110. In an exhaust system, the urea solution is sprayed to a catalyst unit by the urea solution sprayer disposed in immediately upstream side of an exhaust gas purification catalyst unit.

The liquid type identifying device 104 has an identifying sensor section (identifying sensor unit) 2 and support portion 4. The identifying sensor section 2 is attached to one end (lower end) of the support portion 4, and an attachment portion 4a for attachment to the tank opening 102 is attached to the other end (upper end) of the support portion 4.

Figure 4:
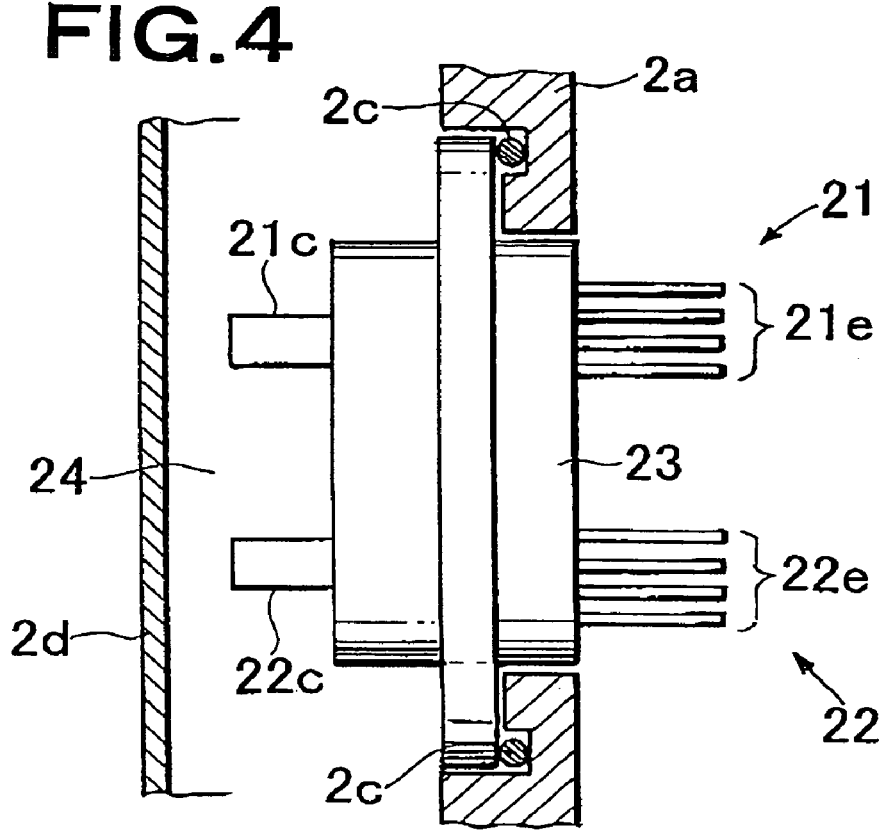
FIG. 4 is an enlarged view showing an indirect-heating liquid type detection section and a liquid temperature detecting section.
Figure 5:
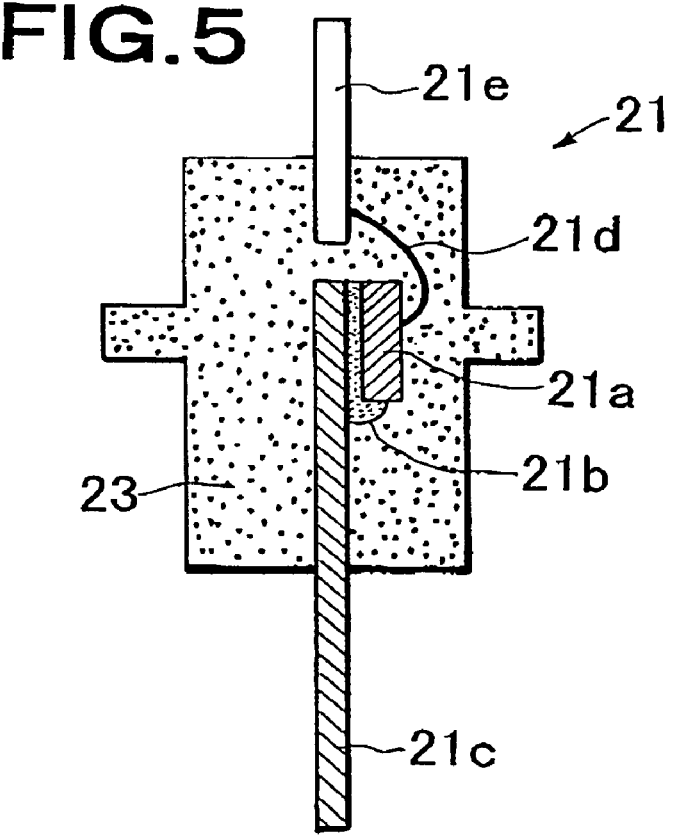
FIG. 5 is a cross-sectional view showing the indirect-heating liquid type detection section of FIG. 4.

The identifying sensor section 2 has an indirect-heating liquid type detection section 21 including a heater and temperature sensor (heat sensor) and a liquid temperature detecting section (liquid temperature sensing section) 22 for detecting the temperature of a liquid to be measured. The indirect-heating liquid type detection section 21 and liquid temperature detecting section 22 are disposed apart from each other in vertical direction by a predetermined interval. FIG. 4 shows, in an enlarged manner, the indirect-heating liquid type detection section 21 and liquid temperature detecting section 22. FIG. 5 shows a cross-section of FIG. 4.

As shown in FIGS. 4 and 5, the indirect-heating liquid type detection section 21 and liquid temperature detecting section 22 are integrated with each other by means of mold resin 23. As shown in FIG. 5, the indirect-heating liquid type detection section 21 has a thin-film chip 21a including the heater and temperature sensor, a metal fin 21c serving as a heat transfer member for liquid type detection section, which is coupled to the thin-film chip 21a by means of a bonding material 21b, and an external electrode terminal 21e electrically connected respectively to electrodes of the heater and temperature sensor of the thin-film chip 21a by means of a bonding wire 21d. The liquid temperature detecting section 22, which has the same configuration as that of the indirect-heating liquid type detection section 21, has a metal fin 22c serving as a heat transfer member for liquid temperature detecting section and an external electrode terminal 22e.

Figure 6:
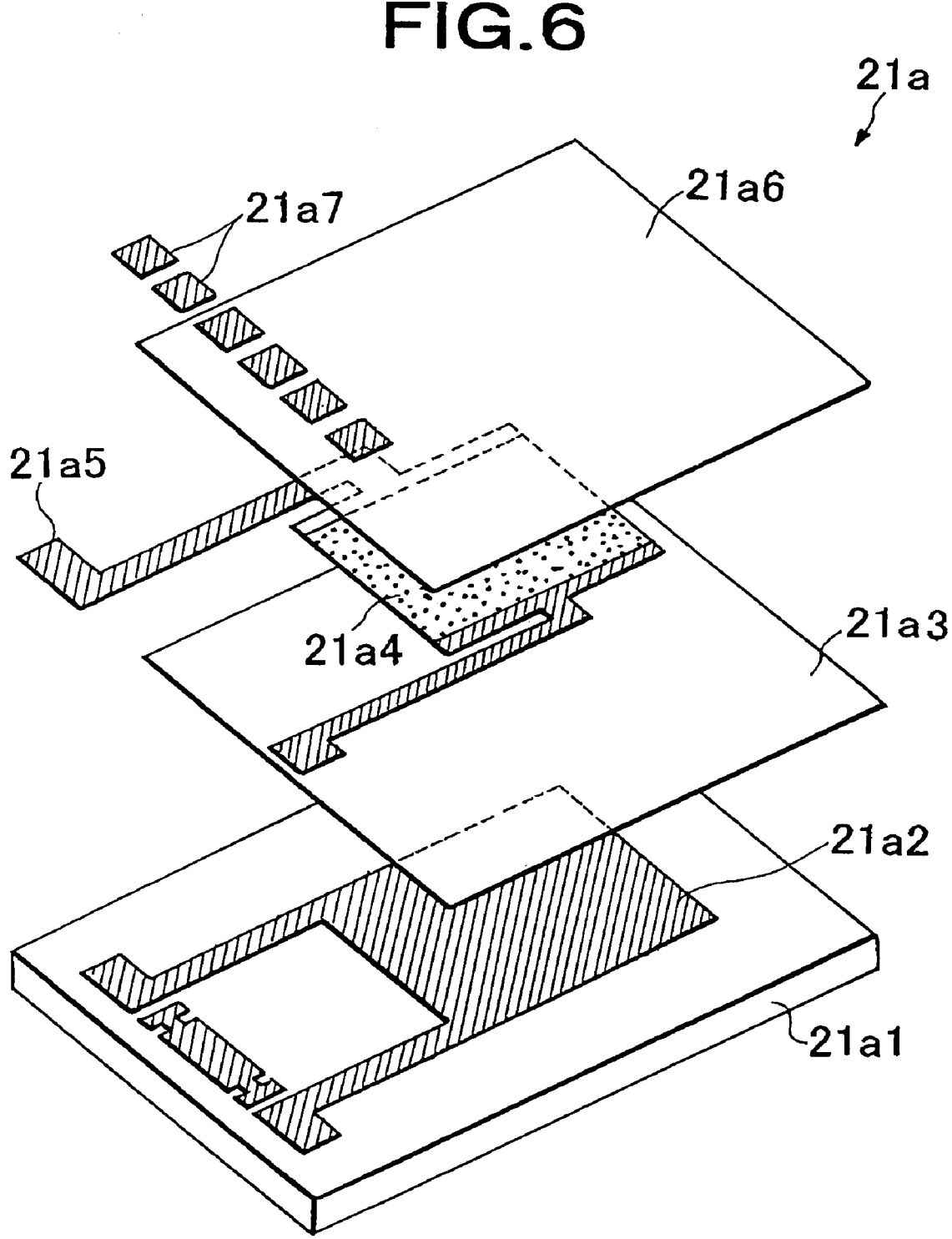
FIG. 6 is an exploded perspective view showing a thin-film chip of the indirect-heating liquid type detection section.

FIG. 6 is an exploded perspective view showing the thin-film chip 21a of the indirect-heating liquid type detection section 21. The thin-film chip 21*a* has a laminated body in which, for example, a substrate 21*a*1 made of $Al_2O_3$, a temperature sensor 21*a*2 made of Pt, an interlayer dielectric film 21*a*3 made of $SiO_2$, a heater 21*a*4 made of $TaSiO_2$, a heater electrode 21*a*5 made of Ni, a protection film 21*a*6 made of $SiO_2$, and an electrode pad 21*a*7 made of Ti/Au are sequentially laminated. Although not shown, the temperature sensor 21*a*2 is formed in a zig-zag pattern. Although a thin-film chip 22*a* of the liquid temperature detecting section 22 has the same configuration as that of the thin-film chip 21*a* of the indirect-heating liquid type detection section 21, it does not allow the heater to be active, but allows only a temperature sensor 22*a*2 to be active.

As shown in FIGS. 1 and 2, the identifying sensor section 2 has a base body 2*a* attached to the lower end of the support portion 4. When the base body 2 is attached to the support portion 4, O-rings 2*b* are interposed therebetween. A mold resin 23 integrating the indirect-heating liquid type detection section 21 and liquid temperature detecting section 22 is attached to the side surface of the base body 2*a* through an O-ring 2*c*. A cover member 2*d* is so provided to the base body 2*a* as to surround the metal fin 21*c* for liquid type detection section and metal fin 22*c* for liquid temperature detecting section. In a state where the cover member 2*d* has been attached to the base body 2*a*, an introduction passage 24 for liquid to be measured is formed. The introduction passage 24 extends, passing through the metal fin 21*c* for liquid type detection section and metal fin 22*c* for liquid temperature detecting section, in a vertical direction with its upper and lower ends opened. Further, in a state where the cover member 2*d* has been attached to the base body 2*a*, the flange portion of the mold resin 23 is pressed against the base body 2*a* to cause the mold resin 23 to be fixed to the base body 21*a*.

A circuit substrate 6 that constitutes a liquid type detecting circuit to be described later is disposed on the upper end of the support portion 4. A cover member 8 is so attached to the upper end of the support portion 4 as to cover the circuit substrate 6. As shown in FIG. 2, a wiring 10 electrically connecting the indirect-heating liquid type detection section 21 and liquid temperature detecting section 22 of the identifying sensor section 2 to the circuit substrate 6 extends inside the support portion 4. A microcomputer that constitutes an identifying calculation section to be described later is mounted on the circuit substrate 6. A wiring 14 extends between the circuit substrate 6 and an external device through a connector 12 provided to the cover member 8 for communication between them. The identifying calculation section may be disposed outside the circuit substrate 6. In this case, the circuit substrate 6 and identifying calculation section are connected through the wiring 14.

The above-mentioned base body 2*a* and cover member 2*d* of the identifying sensor section 2, support portion 4, and cover member 8 are made of a corrosion-resistant material such as a stainless steel.

Figure 7:
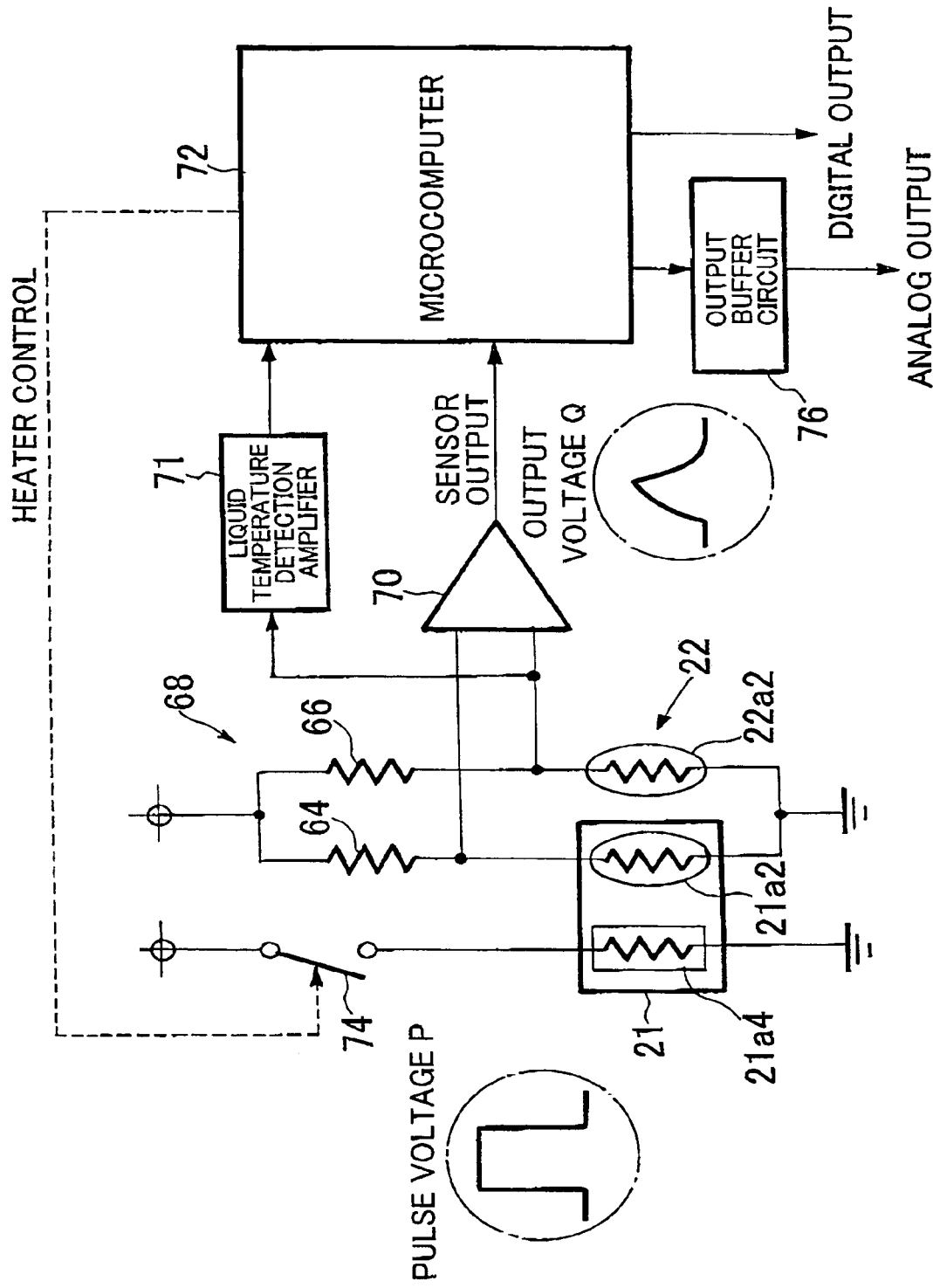
FIG. 7 is a diagram showing a configuration of a circuit for liquid identification.

FIG. 7 shows a configuration of a circuit for liquid identification performed in the present embodiment. The temperature sensor 21*a*2 of the indirect-heating liquid type detection section 21, temperature sensor 22*a*2 of the liquid temperature detecting section 22, and two resistors 64, 66 constitute a bridge circuit 68. The output of the bridge circuit 68 is input to a differential amplifier 70, and the output of the differential amplifier 70 (also referred to as "liquid type detecting circuit output" or "sensor output") is input to the microcomputer 72 that constitutes an identifying calculation section through a not shown A/D converter. Further, to the microcomputer 72, a liquid-temperature-corresponding output value which correspond to the temperature of a liquid to be measured is input from the temperature sensor 22*a*2 of the liquid temperature detecting section 22 through a liquid temperature detecting amplifier 71. Further, a heater control signal for controlling open/close of a switch 74 is output from the microcomputer 72 to the switch 74 disposed in a power supplying line to the heater 21*a*4 of the indirect-heating liquid type detection section 21.

A liquid type identifying operation in the present embodiment will be described below.

Firstly, the tank 100 is filled with a liquid to be measured US and, at the same time, the introduction passage 24 for liquid to be measured, which is formed by the cover member 2*d* of the identifying sensor section 2, is filled with the liquid to be measured US. The liquid to be measured US supplied in the tank 100 and introduction passage 24 for liquid to be measured does not substantially flow.

The switch 74 is closed for a predetermined time period (e.g., 8 seconds) by means of the heater control signal output from the microcomputer 72 to the switch 74. Then, a single pulse voltage P having a predetermined height (e.g., 10V) is applied to the heater 21*a*4 to allow the heater to generate heat. An output voltage (sensor output) Q of the differential amplifier 70 at that time gradually increases while a voltage is applied to the heater 21*a*4 and gradually decreases after the voltage application to the heater 21*a*4 is ended, as shown in FIG. 8.

Figure 8:
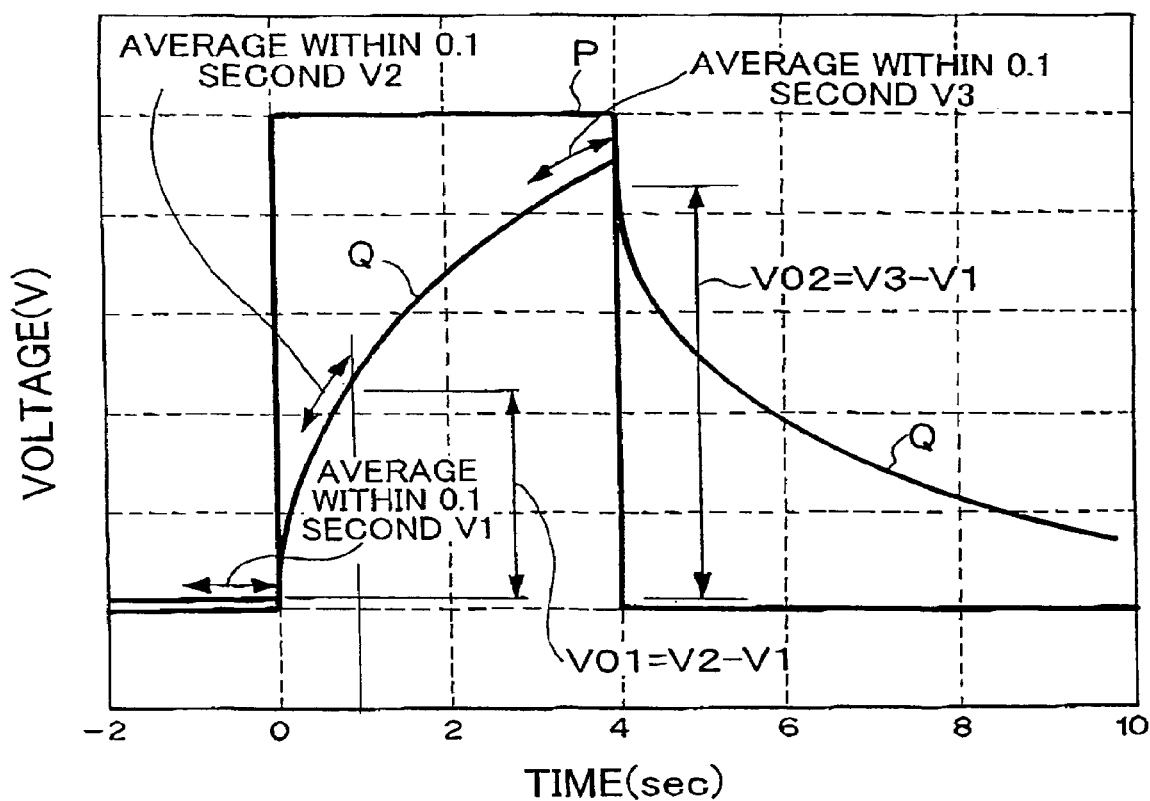
FIG. 8 is a diagram showing a relationship between a single pulse voltage P applied to a heater and sensor output Q.

As shown in FIG. 8, the microcomputer 72 samples the sensor outputs for a predetermined time period (e.g., 0.1 seconds) before the start of voltage application to the heater 21*a*4 a predetermined number of times (e.g., 256 times) and performs calculation for obtaining the average value of the sensor outputs to thereby obtain an average initial voltage value V1. The average initial voltage value V1 corresponds to the initial temperature of the temperature sensor 21*a*2.

Further, as shown in FIG. 8, the microcomputer 72 samples the sensor outputs at the time point after a first time period (e.g., ½ or less of the single pulse application time (e.g., 0.5 to 3 seconds; 2 seconds in FIG. 8)), which is comparatively short time period, has elapsed from the start of the voltage application to the heater (specifically, immediately before the elapse of the first time) a predetermined number of times (e.g., 256 times) and performs calculation for obtaining the average value of the sensor outputs to thereby obtain an average first voltage value V2. The average first voltage value V2 corresponds to a first temperature of the temperature sensor 21*a*2, which is obtained at the time point after the first time period has elapsed from the start of the single pulse application. Then, a difference V01 (=V2−V1) between the average initial voltage value V1 and average first voltage value V2 is obtained as a liquid-type-corresponding first voltage value.

Further, as shown in FIG. 8, the microcomputer 72 samples the sensor outputs at the time point after a second time period (e.g., single pulse application time (8 seconds in FIG. 8)), which is comparatively long time period, has elapsed from the start of the voltage application to the heater (specifically, immediately before the elapse of the second time) a predetermined number of times (e.g., 256 times) and performs calculation for obtaining the average value of the sensor outputs to thereby obtain an average second voltage value V3. The average second voltage value V3 corresponds to a second temperature of the temperature sensor 21*a*2, which is obtained at the time point after the second time period has elapsed from the start of the single pulse application. Then, a difference V02 (=V3−V1) between the average initial voltage value V1 and average second voltage value V3 is obtained as a liquid-type-corresponding second voltage value.

A part of the heat generated in the heater 21a4 at the time of the single pulse voltage application is transferred to the temperature sensor 21a2 through the liquid to be measured. This heat transfer consists primarily of two modes which differ from each other depending on the time from the start of the pulse application. That is, at a first stage within a comparatively short time period (e.g., 3 seconds, especially 2 seconds) from the start of the pulse application, the heart transfer is mainly controlled by conduction (therefore, the liquid-type-corresponding first voltage value V01 is mainly influenced by the heat conductivity of a liquid). At a second stage after the first stage, the heat transfer is mainly controlled by natural convection (therefore, the liquid-type-corresponding second voltage value V02 is mainly influenced by the kinetic viscosity of a liquid). It is because that, at the second stage, the natural convection occurs by the liquid heated at the first stage so that rate of the heat transfer by the natural convection increases.

As described above, it is considered that the optimum concentration [percent by weight (this is the same in the following description)] of the urea solution used in the exhaust gas purification system is 32.5%. Therefore, the allowable range of the urea concentration of the urea solution to be stored in the urea solution tank 100 can be set to, e.g., 32.5%±5%. The value (±5%) of the allowable range may appropriately be changed. That is, in the present embodiment, the urea solution having a urea concentration of 32.5±5% is defined as a predetermined solution.

The liquid-type-corresponding first voltage value V01 and liquid-type-corresponding second voltage value V02 change as the urea concentration of the urea solution changes. Therefore, a range (predetermined range) of the liquid-type-corresponding first voltage value V01 and a range (predetermined range) of liquid-type-corresponding second voltage value V02, which correspond to the urea solution having a urea concentration of 32.5±5%, exist.

Figure 9:
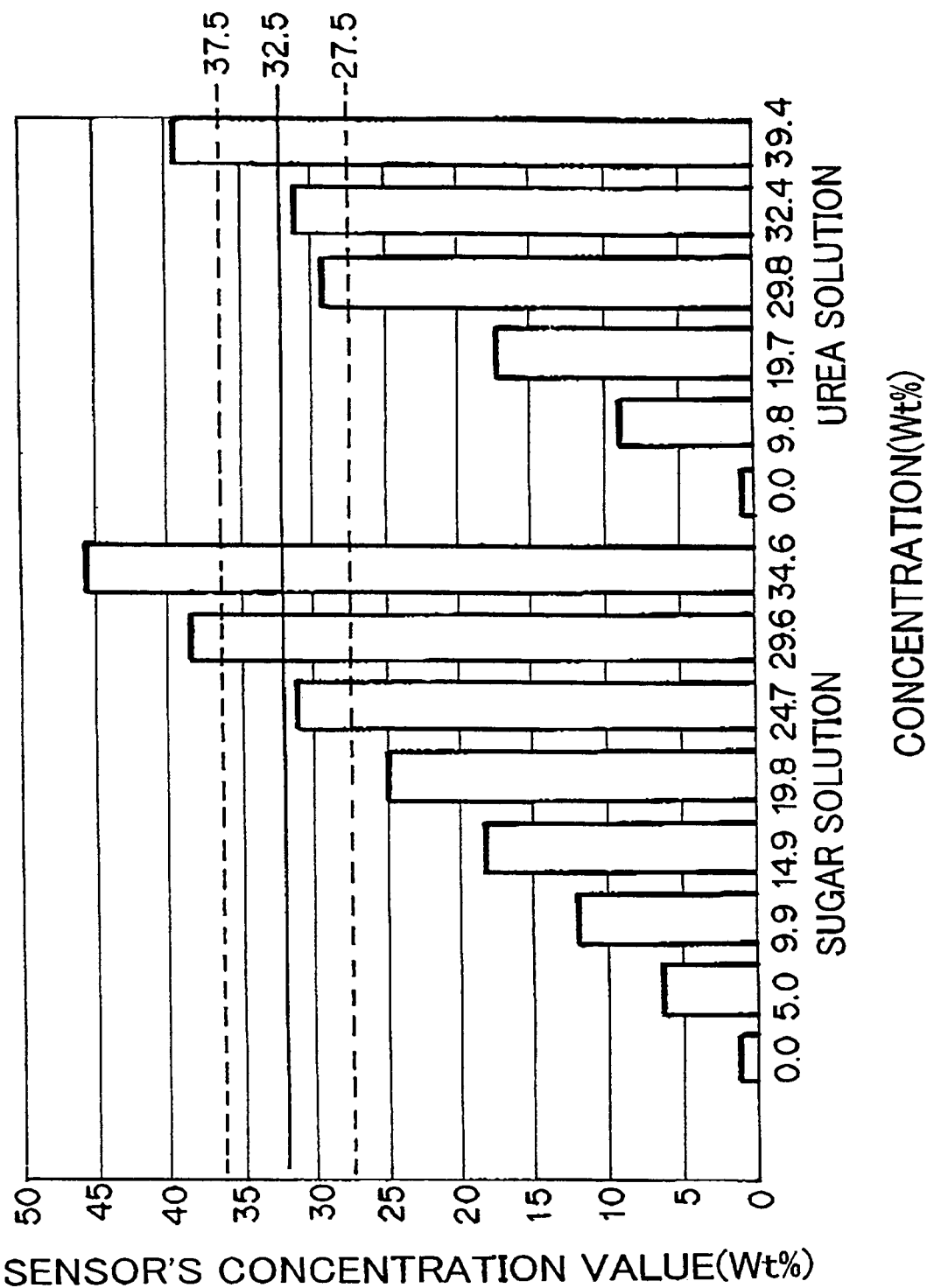
FIG. 9 is a diagram indicating that the liquid-type-corresponding first voltage value obtained using sugar solution having a certain sugar concentration exists within the range of the liquid-type-corresponding first voltage value V01 obtained using urea solution having a urea concentration falling within a predetermined range.

Even in the case of a liquid other than the urea solution, an output within a predetermined range of the liquid-type-corresponding first voltage value V01 and output within a predetermined range of the liquid-type-corresponding second voltage value V02 may be obtained in some cases, depending on its concentration. In other words, even when the liquid-type-corresponding first voltage value V01 or liquid-type-corresponding second voltage value V02 falls within its predetermined range, a liquid to be measured is not always the predetermined urea solution. For example, as shown in FIG. 9, the liquid-type-corresponding first voltage value of sugar solution having a sugar concentration of about 25%±3% exists within the range of the liquid-type-corresponding first voltage value V01 obtained using the urea solution having a urea concentration falling within the predetermined range of 32.5%±5% (i.e., within a range of 32.5%±5% in terms of the sensor's concentration value).

Figure 10:
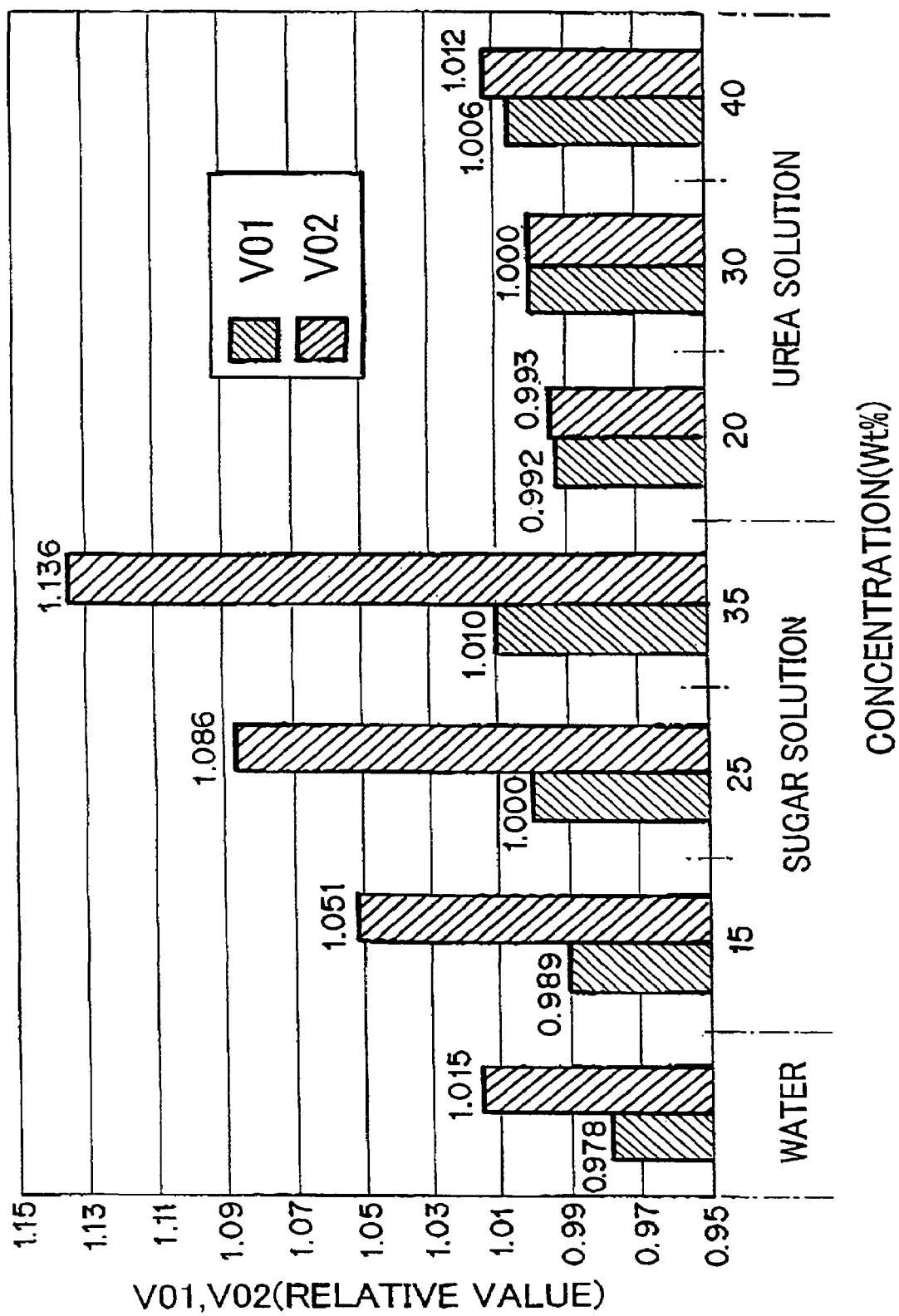
FIG. 10 is a diagram in which both of the liquid-type-corresponding first voltage value V01 and liquid-type-corresponding second voltage value V02 obtained with respect to the urea solution, sugar solution and water are represented by a relative value when the respective values V01 and V02 of the urea solution having a urea concentration of 30% are set to 1.000.

However, the value of liquid-type-corresponding second voltage value V02 obtained using the sugar solution having the above sugar concentration becomes largely different from the liquid-type-corresponding second voltage value V02 obtained using the urea solution having a urea concentration falling within the predetermined range. That is, as shown in FIG. 10, although some sugar solutions having a sugar concentration falling within a range of 15% to 35%, including sugar concentration range of the above 25%±3%, overlap with the urea solutions having a urea concentration falling within the predetermined range in terms of the liquid-type-corresponding first voltage value V01, they largely differ from the urea solutions having a urea concentration falling within the predetermined range in terms of the liquid-type-corresponding second voltage value V02. Note that, in FIG. 10, both of the liquid-type-corresponding first voltage value V01 and liquid-type-corresponding second voltage value V02 are represented by a relative value when the values V01 and V02 of the urea solution having a urea concentration of 30% are set to 1.000. That is, by making a determination whether the solution to be identified is a predetermined solution based on whether the solution to be identified falls within a predetermined range in terms of both the liquid-type-corresponding first voltage value V01 and liquid-type-corresponding second voltage value V02, it is possible to certainly determine that the sugar solution is not a predetermined solution.

Further, a liquid other than a predetermined solution may overlap with the predetermined solution in terms of the liquid-type-corresponding second voltage value V02 in some cases. However, in this case, a liquid to be measured differs from the predetermined solution in terms of the liquid-type-corresponding first voltage value V01, so that it is possible to certainly determine that the liquid to be measured is not a predetermined solution by the above determination.

As described above, in the present invention, identification of the liquid type is performed based on the fact that solutions differ from each other in terms of a combination of the liquid-type-corresponding first voltage value V01 and liquid-type-corresponding second-voltage value V02. That is, the liquid-type-corresponding first voltage value V01 and liquid-type-corresponding second voltage value V02 are influenced by different properties, i.e., heat conductivity and kinetic viscosity, so that the combination of the liquid-type-corresponding first voltage value V01 and liquid-type-corresponding second voltage value V02 varies depending on the solution type, which enables the liquid identification as described above. By narrowing the predetermined range of the urea concentration, it is possible to further increase the identification accuracy.

Figure 11:
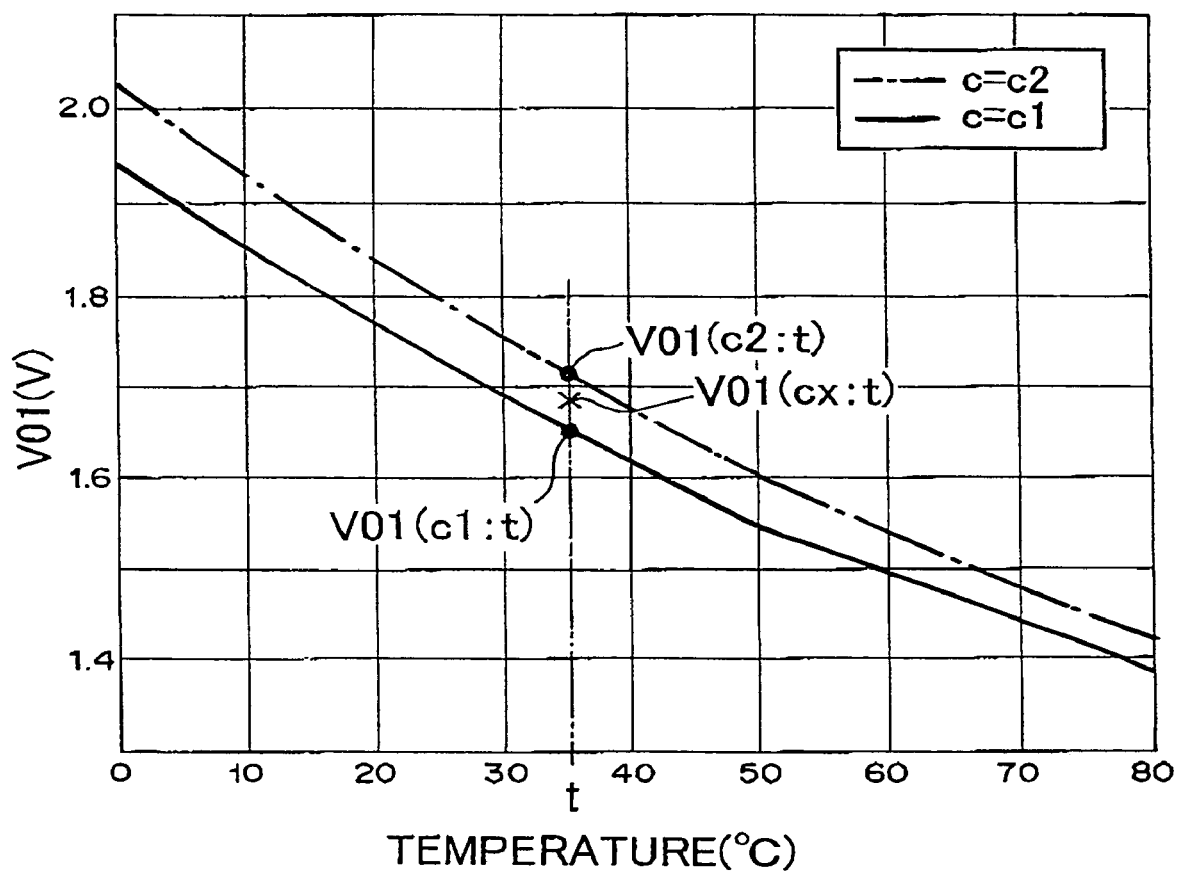
FIG. 11 is a diagram showing an example of a first calibration curve.
Figure 12:
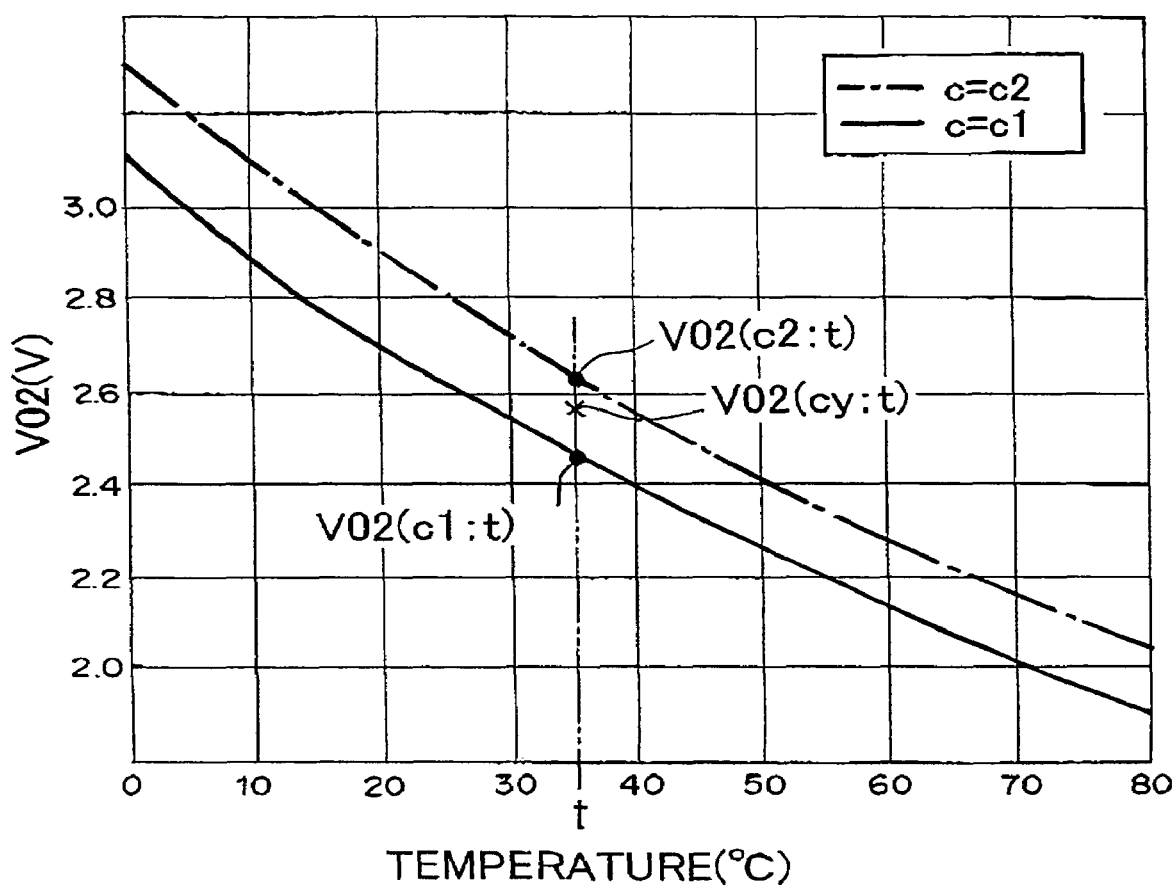
FIG. 12 is a diagram showing an example of a second calibration curve.

In the embodiment of the present invention, a first calibration curve indicating a relationship between the temperature and liquid-type-corresponding first voltage value V01 and a second calibration curve indicating a relationship between the temperature and liquid-type-corresponding second voltage value V02 are previously obtained with respect to some urea solutions (reference urea solutions) each having a known urea concentration, and these calibration curves are stored in a storage means of the microcomputer 72. FIGS. 11 and 12 show examples of the first and second calibration curves, respectively. In these examples, the calibration curves of reference urea solutions having urea concentrations c1 (e.g., 27.5%) and c2 (e.g., 37.5%) are shown.

Figure 13:
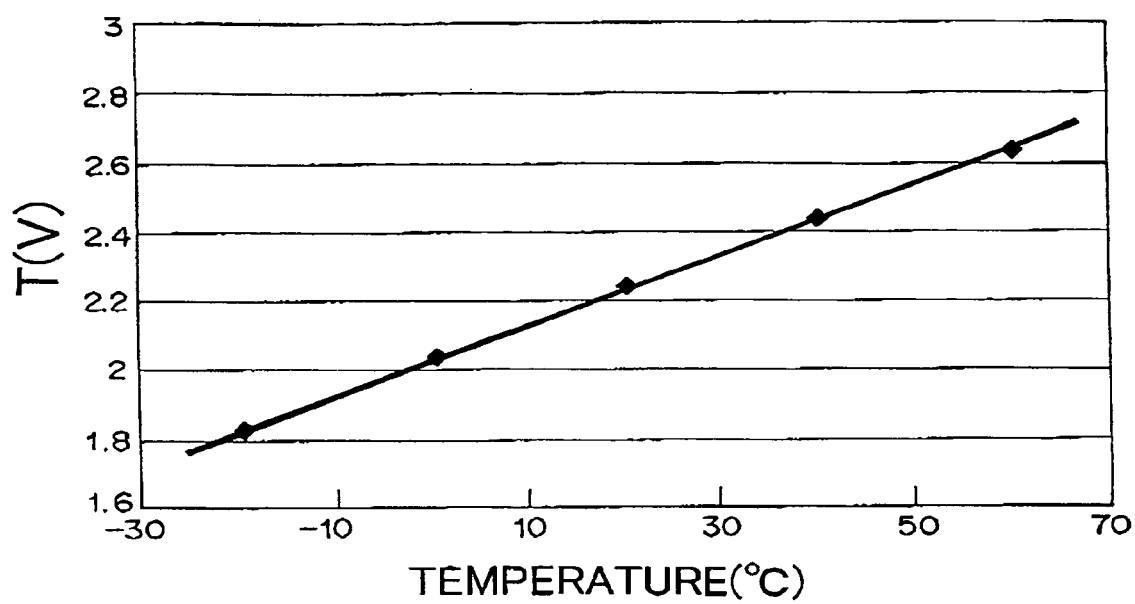
FIG. 13 shows an example of a liquid-temperature-corresponding output value T.

As shown in FIGS. 11 and 12, the liquid-type-corresponding first voltage value V01 and liquid-type-corresponding second voltage value V02 change depending on the temperature, so that when these calibration curves are used to identify a liquid to be measured, a liquid-temperature-corresponding output value T which is input from the temperature sensor 22a2 of the liquid temperature detecting section 22 through the liquid temperature detecting amplifier 71 is also used. FIG. 13 shows an example of the liquid-temperature corresponding output value T. Such a calibration curve is also stored in the storage means of the microcomputer 72.

When the liquid-type-corresponding first voltage value V01 is measured, a temperature value is first obtained from the liquid-temperature-corresponding output value T of the liquid to be measured with reference to the calibration curve of FIG. 13. The obtained temperature value is set as t. Then, on the first calibration curve of FIG. 11, the liquid-type-corresponding first voltage values V01(c1;t) and V01(c2;t) of the respective calibration curves which correspond to the temperature value t are obtained. Subsequently, cx of the liquid-type-corresponding first voltage value V01(cx;t) obtained with respect to the liquid to be measured is determined by performing proportional calculation using the liquid-type-corresponding first voltage values V01(c1;t) and V01(c2;t) of the respective calibration curves. That is, cx is calculated from the following equation (1) based on V01(cx;t), V01(c1;t), and V01(c2;t):

$$cx = c1 + (c2-c1)[V01(cx;t) - V01(c1;t)]/[V01(c2;t) - V01(c1;t)] \quad (1)$$

Similarly, when the liquid-type-corresponding second voltage value V02 is measured, the liquid-type-corresponding second voltage values V02(c1;t) and V02(c2;t) of the respective calibration curves which correspond to the temperature value t, which has been obtained as described above, are obtained on the second calibration curve of FIG. 12. Subsequently, cy of the liquid-type-corresponding second voltage value V02(cy;t) obtained with respect to the liquid to be measured is determined by performing proportional calculation using the liquid-type-corresponding second voltage values V02(c1;t) and V02(c2;t) of the respective calibration curves. That is, cy is calculated from the following equation (2) based on V01(cy;t), V01(c1;t), and V01(c2;t):

$$cy = c1 + (c2-c1)[V02(cy;t) - V02(c1;t)]/[V02(c2;t) - V02(c1;t)] \quad (2)$$

When the first and second calibration curves of FIGS. 11 and 12 are created based on the liquid-temperature-corresponding output value T in place of the temperature, the storage of the calibration curve of FIG. 13 and conversion using the same can be omitted.

As described above, a predetermined range that changes depending on the temperature can be set with respect, respectively, to the liquid-type-corresponding first voltage value V01 and liquid-type-corresponding second voltage value V02. By setting c1 to 27.5% and c2 to 37.5% as described above, it can be seen that a region between the two calibration curves in each of FIGS. 11 and 12 corresponds to the predetermined liquid (i.e., urea solution having a urea concentration of 32.5%±5%).

Figure 14:
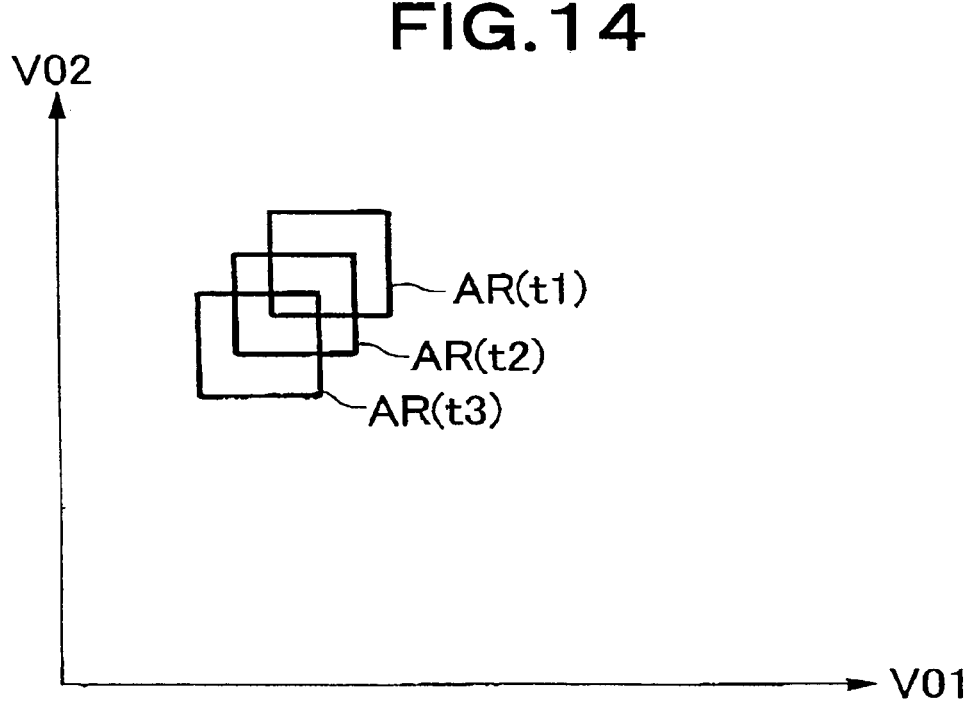
FIG. 14 is a graph schematically showing that criteria of the determination whether the liquid to be measured is a predetermined liquid, which is performed using the combination of liquid-type-corresponding first voltage value V01 and liquid-type-corresponding second voltage value V02, changes depending on the temperature.

FIG. 14 is a graph schematically showing that the criteria of the determination whether the liquid to be measured is a predetermined liquid, which is performed using the combination of liquid-type-corresponding first voltage value V01 and liquid-type-corresponding second voltage value V02, changes depending on the temperature. As the temperature rises (t1, t2, t3 in this order), a region in which a liquid to be measured is determined to be a predetermined liquid is moved (AR(t1), AR(t2), AR(t3) in this order).

Figure 15:
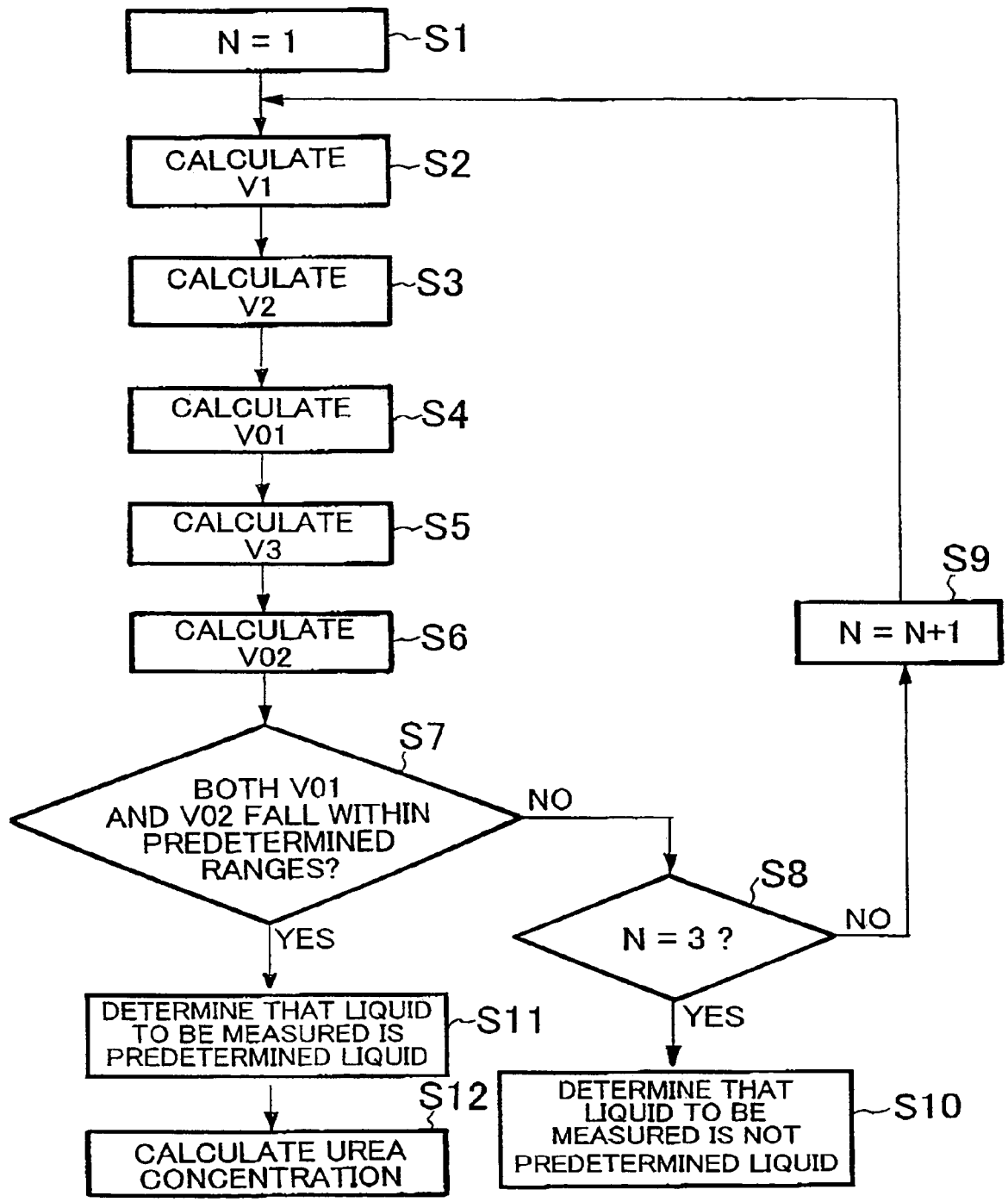
FIG. 15 is a flowchart showing a liquid identifying process, wherein reference numeral 2 denotes a liquid-type identifying sensor section, 2a base body, 2b,2c O-ring, 2d cover member, 21 indirect-heating liquid type detection section, 22 liquid temperature detecting section, 23 mold resin, 24 introduction passage for liquid to be measured, 21a thin-film chip, 21b bonding material, 21c,22c metal fin, 21d bonding wire, 21e,22c external electrode terminal, 21a1 substrate, 21a2, 22a2 temperature sensor, 21a3 interlayer dielectric film, 21a4 heater, 21a5 heater electrode, 21a6 protection film, 21a7 electrode pad, 4 support portion, 4a attachment portion, 6 circuit substrate, 8 cover member, 10,14 wiring, 12 connector, 64,66 resistor, 68 bridge circuit, 70 differential amplifier, 71 liquid temperature detecting amplifier, 72 microcomputer, 74 switch, 76 output buffer circuit, 100 urea solution tank, 102 opening, 104 liquid type identifying device, 106 inlet piping, 108 outlet piping, 110 urea solution supply pump, and US denotes a liquid to be measured.

FIG. 15 is a flowchart showing a liquid type identifying process performed by the microcomputer 72.

Firstly, N=1 is stored in the microcomputer 72 (S1) before application of a pulse voltage to the heater 21a4 which is performed under heater control. Then, the microcomputer 72 samples sensor outputs to obtain the average first voltage value V1 (S2). After that, the microcomputer 72 starts heater control and samples sensor outputs at the time after the first time period has elapsed from the start of the voltage application to the heater 21a4 to obtain the average first voltage value V2 (S3). Then, microcomputer 72 calculates V2−V1 to obtain the liquid-type-corresponding first voltage value V01 (S4). Subsequently, microcomputer 72 samples sensor outputs at the time after the second time period has elapsed from the start of the voltage application to the heater 21a4 to obtain the average second voltage value V3 (S5). Then, microcomputer 72 calculates V3−V1 to obtain the liquid-type-corresponding second voltage value V02 (S6).

Then, referring to the temperature value t obtained with respect to the liquid to be measured, the microcomputer 72 determines whether a condition that both the liquid-type-corresponding first voltage value V01 and liquid-type-corresponding second voltage value V02 fall within their respective predetermined ranges at the corresponding temperature is satisfied (S7). When determining in S7 that at least one of the liquid-type-corresponding first voltage value V01 and liquid-type-corresponding second voltage value V02 does not fall within its predetermined range (NO in S7), the microcomputer 72 determines whether the stored value N is 3 (S8). When determining that N is not 3 [i.e., the current measurement routine is not the third routine (specifically, the current routine is the first or second routine)] (No in S8), the microcomputer 72 increases the stored value N by 1 (S9) and returns to S2. On the other hand, when determining in S8 that the stored value N is 3 [i.e., the current measurement routine is the third routine] (YES in S8), the microcomputer 72 determines that the liquid to be measured is not a predetermined one (S10).

On the other hand, when determining in S7 that both the liquid-type-corresponding first voltage value V01 and liquid-type-corresponding second voltage value V02 fall within their respective predetermined ranges (YES in S7), the microcomputer 72 determines that the liquid to be measured is a predetermined one (S11).

In the present embodiment, after S1, the urea concentration of the urea solution is calculated (S12). The urea concentration can be calculated based on the output of the liquid temperature detecting section 22, i.e., temperature t obtained with respect to the liquid to be measured, liquid-type-corresponding first voltage value V01, and first calibration curve of FIG. 11 and by using the above equation (1). Alternatively, the urea concentration can be calculated based on the output of the liquid temperature detecting section 22, i.e., temperature t obtained with respect to the liquid to be measured, liquid-type-corresponding second voltage value V02, and second calibration curve of FIG. 12 and by using the above equation (2).

In the manner as described above, identification of the liquid type can be performed correctly and quickly. The routine of the liquid type identification can appropriately be performed when a car engine starts up, or periodically, or at the time of a request from a driver or car (ECU to be described later), or key-off time. Further, it is possible to monitor in a desired mode whether or not a liquid in the urea solution tank is urea solution having a predetermined urea solution. A signal (signal indicating whether a liquid to be measured is a predetermined one, as well as, the urea concentration, in the case where the liquid to be measured is a predetermined one [=urea solution having a predetermined urea concentration]) indicating the liquid type obtained as described above is output to an output buffer circuit 76 shown in FIG. 7 through a not shown D/A converter. The signal is then output as an analog output from the output buffer circuit 76 to a not shown main computer (ECU) which performs car engine combustion control. An analog output voltage value corresponding to the liquid temperature is also output to the main computer (ECU). A signal indicating the liquid type can be taken out as a digital output according to need, and can be input to a device that performs display, alarm, and other operations.

Further, an alarm may be issued when it is detected that the temperature of the urea solution is decreased near to the freezing temperature (about −13° C.) of the urea solution based on the liquid-temperature-corresponding output value T input from the liquid temperature detecting section 22.

The liquid type identification described above uses natural convection and uses a principle that there is a correlation between the kinetic viscosity of a liquid to be measured such as urea solution and sensor output. In order to enhance the accuracy of the liquid identification, it is preferable to make a forced flow due to an external factor less likely to occur in the liquid to be measured around the fin 21c for liquid type detection section and fin 22c for liquid temperature detecting section. In this regard, it is preferable to use the cover member 2d, especially, one that forms the vertical introduction passage for liquid to be measured. The cover member 2d functions also as a protection member for preventing foreign matters from contacting the indirect-heating liquid type detection section 21 and liquid temperature detecting section 22.

Although the urea solution having a predetermined urea concentration is used as a predetermined fluid in the embodiment described above, a predetermined liquid may be a solution using a dissolved substance other than urea or other liquids.

What is claimed is:

1. A liquid type identifying method, which identifies whether or not a liquid to be measured which is an aqueous solution contains a predetermined solute by sensing heat generated by energization with a temperature sensor, the identification of whether or not the liquid to be measured contains a predetermined solute being made based on a combination of a liquid-type-corresponding first voltage value corresponding to a difference between an initial temperature of the temperature sensor and a first temperature thereof obtained at the time point after a first time period has elapsed from a start of the energization and a liquid-type-corresponding second voltage value corresponding to a difference between the initial temperature of the temperature sensor and a second temperature thereof obtained at the time point after a second time period, which is longer than the first time period, has elapsed from the start of the energization.

2. The liquid type identifying method as set forth in claim 1, wherein the predetermined solute is a urea.

3. The liquid type identifying method as set forth in claim 1, wherein the liquid-type-corresponding first voltage value and liquid-type-corresponding second voltage value are obtained based on outputs of a liquid type detecting circuit including both the temperature sensor and a liquid temperature detecting section for detecting a temperature of the liquid to be measured.

4. The liquid type identifying method as set forth in claim 1, wherein an average initial voltage value which is obtained by sampling an initial voltage predetermined number of times before the start of energization to the heater and averaging them is used as a voltage value corresponding to the initial temperature of the temperature sensor, an average first voltage value which is obtained by sampling a first voltage at the time after the first time period has elapsed from the start of energization to the heater predetermined number of times and averaging them is used as a voltage value corresponding to the first temperature of the temperature sensor, an average second voltage value which is obtained by sampling a second voltage at the time after the second time period has elapsed from the start of energization to the heater predetermined number of times and averaging them is used as a voltage value corresponding to the second temperature of the temperature sensor, a difference between the average first voltage value and average initial voltage value is used as the liquid-type-corresponding first voltage value, and a difference between the average second voltage value and average initial voltage value is used as the liquid-type-corresponding second voltage value.

5. The liquid type identifying method as set forth in claim 1, which identifies whether or not the liquid to be measured which is an aqueous solution contains a predetermined solute in a predetermined concentration based on a combination of the liquid-type-corresponding first voltage value and the liquid-type-corresponding second voltage value.

6. The liquid type identifying method as set forth in claim 5, wherein a first calibration curve or second calibration curve indicating a relationship between the temperature and liquid-type-corresponding first voltage value or liquid-type-corresponding second voltage value with respect to urea solutions having different urea concentrations is prepared and, when the liquid to be measured is determined to be urea solution having a urea concentration falling within a predetermined range, the urea concentration of the urea solution is calculated based on an output of a liquid temperature detecting section for detecting the temperature of the liquid to be measured, liquid-type-corresponding first voltage value or liquid-type-corresponding second voltage value, and first or second calibration curve.

7. The liquid type identifying method as set forth in claim 5, wherein it is determined that the liquid to be measured is an aqueous urea solution containing urea in a predetermined concentration only when both the liquid-type-corresponding first voltage value and liquid-type-corresponding second voltage value fall within respective predetermined ranges and, otherwise, it is determined that the liquid to be measured is not an aqueous urea solution containing urea in a predetermined concentration.

8. The liquid type identifying method as set forth in claim 7, wherein the predetermined range of the liquid-type-corresponding first voltage value and that of the liquid-type-corresponding second voltage value change depending on a temperature of the liquid to be measured.

9. The liquid type identifying method as set forth in claim 1, wherein the energization is applied by applying a single pulse voltage and the heat generated by the energization is transferred through the liquid to be measured to the temperature sensor disposed to face the liquid.

10. The liquid type identifying method as set forth in claim 9, wherein the single pulse voltage is applied to a heater disposed to face the liquid to be measured.

11. A liquid type identifying device, which identifies whether or not a liquid to be measured which is an aqueous solution contains a predetermined solute by sensing heat generated by energization with a temperature sensor, the device comprising:

an identifying sensor section disposed to face a flow passage of the liquid to be measured, the identifying sensor section having both a liquid type detection section including the temperature sensor and a liquid temperature detecting section for detecting the temperature of the liquid to be measured; and an identifying calculation section which identifies the type of the liquid to be measured based on outputs of a liquid type detecting circuit including both the temperature sensor and the liquid temperature detecting section, wherein the identifying calculation section determines whether or not the liquid to be measured is an aqueous solution of a predetermined solute based on a combination of a liquid-type-corresponding first voltage value corresponding to a difference between an initial temperature of the temperature sensor and a first temperature thereof obtained at the time point after a first time period has elapsed from a start of the energization and a liquid-type-corresponding second voltage value corresponding to a difference between the initial temperature of the temperature sensor and a second temperature thereof obtained at the time point after a second time period, which is longer than the first time period, has elapsed from the start of the energization.

12. The liquid type identifying device as set forth in claim 11, wherein the predetermined solute is a urea.

13. The liquid type identifying device as set forth in claim 11, wherein the liquid type detection section and liquid temperature detecting section have a heat transfer member for liquid type detection section and a heat transfer member for liquid temperature detecting section for heat exchange with the liquid to be measured, respectively.

14. The liquid type identifying device as set forth in claim 11, wherein the identifying calculation section determines whether or not the liquid to be measured which is an aqueous solution contains a predetermined solute in a predetermined concentration based on a combination of the liquid-type-corresponding first voltage value and the liquid-type-corresponding second voltage value.

15. The liquid type identifying device as set forth in claim 14, wherein a liquid-temperature-corresponding output value corresponding to the temperature of the liquid to be measured is input from the liquid temperature detecting section to the identifying calculation section, and the identifying calculation section uses a first calibration curve or second calibration curve indicating a relationship between the temperature of the liquid to be measured and liquid-type-corresponding first voltage value or liquid-type-corresponding second voltage value with respect to urea solutions having different urea concentrations to calculate the urea concentration of the urea solution assuming that the liquid to be measured is the urea solution having a urea concentration falling within a predetermined range, and wherein the urea concentration is calculated based on the liquid-temperature-corresponding output value obtained with respect to the liquid to be measured, liquid-type-corresponding first voltage value or liquid-type-corresponding second voltage value, and first or second calibration curve.

16. The liquid type identifying device as set forth in claim 11, wherein the energization is applied by applying a single pulse voltage and the heat generated by the energization is transferred through the liquid to be measured to the temperature sensor disposed to face the liquid.

17. The liquid type identifying device as set forth in claim 16, wherein the identifying sensor section includes a heater, and the single pulse voltage is applied to the heater.

* * * * *